United States Patent [19]
Schäfer et al.

[11] Patent Number: 5,662,652
[45] Date of Patent: Sep. 2, 1997

[54] BONE SURGERY HOLDING APPARATUS

[75] Inventors: Bernd Schäfer, Schorndorf; Klaus Zielke, Bad Wildungen; Günther Rehder, Winterbach, all of Germany

[73] Assignee: Schafer micomed GmbH, Schorndorf, Germany

[21] Appl. No.: 430,900

[22] Filed: Apr. 27, 1995

[30] Foreign Application Priority Data

Apr. 28, 1994 [DE] Germany ............... 44 14 781.3
Jul. 19, 1994 [DE] Germany ............... 44 25 392.3

[51] Int. Cl.⁶ ................................................ A61B 17/70
[52] U.S. Cl. ............................. 606/61; 606/69; 606/73
[58] Field of Search ......................... 606/61, 60, 69, 606/70, 71, 72, 73

[56] References Cited

U.S. PATENT DOCUMENTS

| | | | |
|---|---|---|---|
| 4,289,123 | 9/1981 | Dunn | 128/84 |
| 5,000,166 | 3/1991 | Karpf | 128/69 |
| 5,133,717 | 7/1992 | Chopin | 606/61 |
| 5,147,360 | 9/1992 | Dubousset | 606/61 |

FOREIGN PATENT DOCUMENTS

0 443 894 A1  8/1991  European Pat. Off. .
9314294 U     3/1994  Germany .

*Primary Examiner*—Michael Buiz
*Assistant Examiner*—David O. Reip
*Attorney, Agent, or Firm*—Jones, Tullar & Cooper, P.C.

[57] ABSTRACT

In a bone surgery holding device for a fixing rod, with a bone plate, which can be fastened to the bone, a receiving device, and a fixing device, which secures the fixing rod in the receiving device, the bone plate has a contact face essentially made to fit the surface of the bone and the fixing rod can be inserted into the receiving device.

42 Claims, 6 Drawing Sheets

BONE SURGERY HOLDING APPARATUS

BACKGROUND OF THE INVENTION

The present invention relates to a bone surgery holding apparatus for a fixing rod, with a bone plate which can be fastened to the bone, a receiving device for the fixing rod, and a fixing device which secures the fixing rod in the receiving device; the bone plate can be fixed to the bone independently of the receiving device.

EP-A-443 894 discloses a bone plate, which can be fastened, for example to a vertebra, via two bone screws. One of the bone screws has a forked head, into which a rod can be inserted and fixed. The bone plates can be connected directly to each other via a further rod. A correction of the bone plates embodied in this way is either impossible or very difficult to achieve, since there are no arrangements made for fastening a correction rod. In addition, after fixing, the holding apparatuses must be coated with pleura.

It has been found that because of the relatively high construction of this known holding apparatus, under the circumstances, a coating with pleura is either impossible or very difficult to achieve. In many cases synthetic pleura is required for the coating, which is not universally available and besides is very costly.

U.S. Pat. No. 4,289,123 discloses another holding apparatus, which can be placed on vertebrae. This holding apparatus is used as a rule to bridge individual vertebrae, by attaching bone plates to the neighboring vertebrae and connecting them to each other via two threaded rods. From a biomechanical point of view, a holding apparatus of this kind is extremely unstable and costly to fasten and install.

SUMMARY OF THE INVENTION

An object of the present invention, therefore, is to provide an improved a bone surgery holding apparatus of the kind mentioned above in such a way that it has greater stability and a lower structural height compared to known holding apparatuses.

This object is achieved according to the present invention in that the bone plate has a contact face which is essentially made to fit one of the bone surfaces, and after fastening of the bone plate to the bone, the fixing rod can be inserted in the receiving device.

Because the shape of the bone plate is adapted to the bone or the vertebra, it can be fastened without trouble to the vertebra, without its having to be prepared. If the bone plate is fastened to the bone and if the individual bones or vertebrae to be connected to each other are aligned and positioned, then the system can be fixed in a simple manner by the fact that a fixing rod is inserted in the receiving device. This fixing rod does not have to be laterally introduced or screwed in as in the prior art, which in most cases is not possible due to restricted conditions, but can be inserted in the receiving devices provided for this purpose. The fixing rod is fixed in these receiving devices and connects the individual bone plates to each other. The system is primarily stable.

Preferably, the receiving device is embodied as being in one piece with the bone plate. This embodiment has the advantage that the forces of the fixing rod are introduced directly onto the bone plate and from this onto the bone. The stability of the system is essentially increased.

In an improvement, it is provided that the receiving device is embodied as fork-shaped and has two distally protruding legs. These distally protruding legs encompass the fixing rod laterally and hold it securely to the bone plate. A lateral slippage of the correction rod lateral to its longitudinal axis is prevented.

A simple insertion of the correction rod after fastening of the bone plate to the bone and positioning of the individual bones in relation to each other is produced since the receiving device is open distally.

In known holding apparatuses, the bone plate is fastened onto the bone and the individual bones are brought into the desired position via a correction rod. If the individual bones are positioned, then the bone plates are connected to each other via a fixing rod, by means of which the position of the individual bones is fixed. Both the correction rod and the fixing rod remain in the body of the patient.

In the holding apparatus according to the, present invention, it is contemplated that the holding apparatus be provided with a tool engaging device, with which a tool can be used to position the bone plate. The position of the bone is not set, as in the prior art, by screwing on a correction rod and adjusting the position of the bone plate and therefore the position of the bone; instead, a tool provided for this purpose is placed on a tool engaging device. The individual bone plates are aligned in relation to each other via this tool.

The tool engaging device is advantageously formed with two parallel faces, which are provided on the receiving device. A fork-shaped tool can be slipped onto these parallel faces and can be slipped off again after the correction of the plate position. As a result of the embodiment of the holding apparatus according to the present invention, with a tool engaging device, a tool can therefore be slipped on to correct the position of the individual bone plates and can be taken off again after correction is carried out. Thus, no elements which are required for correcting the position of individual vertebrae remain in the body of the patient, except for merely the elements required for fixing. This has the essential advantage that the number of foreign bodies remaining in the body is lower and that, because there are fewer remaining in the body or elements disposed on the bone, coating them with pleura is essentially simpler. As a rule, synthetic pleura is no longer required for the coating. In addition, the structural height of the overall holding apparatus is considerably reduced.

In an improvement, it is provided that each leg of the receiving device is formed by two prongs, which serve as a guide for a fixing plate. The fixing rod is fixed to the bone plate with this fixing plate.

An advantageous empty space exists between the prongs, in which the fixing plate is guided so that it can move in the direction of the bone plate. In this manner, a simple but effective clamping of the fixing rod to the bone plate is brought about. In addition in this manner, the fixing plate itself can be placed onto the fixing rod after the rod is inserted and can be fastened to the bone plate.

After placement, sliding of the fixing plate parallel to the bone plate is prevented because the prongs of the bone plate hold the fixing plate in the horizontal plane. The plate can then merely be slipped orthogonally to the bone plate.

Preferably the fixing plate can be fastened onto the bone plate or on the fixing rod via one or several fastening devices. This occurs once the bone plate assumes the desired position and after the fixing rod is inserted. With the fastening of the fixing plate on the bone plate, it is stably connected to the fixing rod, by means of which primary stability is achieved for the individual vertebrae.

The fastening devices are embodied by two screws, which are fastened in a captive manner to the fixing plate. This has the advantage that immediately after placement of the fixing plate, it can be connected with the bone screw.

The screws are disposed along the longitudinal axis of the fixing plate so that an optimal transfer of forces is achieved from the fixing rod onto the bone plate.

Rotation of the fixing rod in the receiving device is prevented by the fact that the fixing plate, or at least part of it, has profiling on its side oriented toward the fixing rod. The base of the receiving device can likewise be provided with profiling. In the case of longitudinally grooved fixing rods, this profiling has complementary longitudinal grooves.

In a preferred exemplary embodiment, the receiving device is embodied to receive an especially longitudinally grooved correction rod with a 6 mm diameter. The holding apparatus has a height of about 8 mm to 10 mm.

The receiving device is provided between two fastening bores, via which the bone plate can be fastened to the bone. This position has the advantage that the forces introduced from the fixing rod onto the bone plate are introduced essentially evenly onto the bone screws and therefore onto the bones. A decentralized disposition of the receiving device is likewise possible.

Play-free fastening of the bone plate on the bone is attained, because each fastening bore has a conical seat for the bone screws.

Preferably the bone plate is designed to be mirror symmetrical, by means of which an optimal distribution of force is achieved.

The holding apparatus according to the present invention is used among other things in cases that involve tumors, fractures, kyphosis, scoliosis, and spondylolisthesis.

In an improvement of the subject of the present invention, it is provided that the bone plate has a connecting device for a correction instrument, which includes at least one correction rod, for example, and which can be removed after correction and fixing.

Through the bone surgery holding apparatus according to the present invention, the possibility is achieved that to correct the position of the vertebra an instrument can be used that can be removed again after fixing of the bone plate. With the bone surgery holding apparatus according to the present invention, therefore, the bone plate is fastened on the bone to be corrected, e.g. on a vertebra of a spinal column, and the correction instrument is fastened to the bone plate by means of the connecting device so that the position of the bone plate and therefore the position of the bone, e.g. the vertebra, can be corrected via the correction instrument. The size of the correction instrument, or for example of one of the correction rods which can be inserted into the instrument, plays only a secondary role, since the instrument with the correction rod is removed again after fixing. Once the bone plate or the vertebra assumes the desired position, then the position of the bone plate is fixed, for example by means of a fixing rod. After fixing, the correction instrument is removed and the operation can be brought to an end. Therefore merely the bone plate and the elements of the holding apparatus required for fixing the bone plate remain in the body of the patient.

Apart from a low structural volume, the bone surgery holding apparatus according to the present invention has a lower height, width, and length than conventional holding apparatuses, so that on the whole it is more tolerable. Because of the lower structural volume, in particular the lower height, the holding apparatus can more easily be coated with pleura. In addition, the shape of the bone plate, which is made to fit the bone or vertebra, has the advantage that fastening can be carried out without trouble, without the bone having to be prepared. The system is primarily stable because the fixing rod is fastened directly to the bone plate.

Because the correction instrument can be used more than once, the costs of operations are reduced, and the holding apparatus remaining in the body of the patient is relatively small; nor should the lower weight go unmentioned.

In a preferred embodiment, the correction instrument can be inserted via the connecting device. After the holding apparatus is fastened on the bone, the correction instrument can be connected with it in a simple manner by being slipped onto or inserted into it. Time-consuming screw connections are not necessary. The insertion direction of the correction instrument essentially corresponds to the longitudinal direction of the bone plate. In other embodiments, the insertion direction corresponds to the lateral direction or lies diagonal to it. Preferably the insertion direction corresponds to the longitudinal direction of the receiving device for the fixing rod.

In order to achieve a definite position of the correction instrument on the bone plate, the correction instrument has a stop, which serves as an insertion limiter. This stop allows the correction instrument to be slipped onto or inserted into the holding apparatus according to the present invention until the stop contacts the holding apparatus. The correction instrument now assumes a predetermined position and the correction forces can be optimally introduced onto the holding apparatus.

In an exemplary embodiment, the connecting device comprises a first part provided on the correction instrument and a second part provided on the bone plate; both parts constitute, for example, a tongue-and-groove connection or a hole-and-peg connection. Connecting devices embodied in this way guarantee an optimal securing of the correction instrument on the bone plate so that there is no danger of an inadvertent sliding or slippage of the correction instrument.

In another embodiment, it is provided that the connecting device is provided on the receiving device for the fixing rod. Here, the connecting device comprises, for example, two parallel faces. At least one of the faces can be provided with a groove or a projection extending in the insertion direction, which serves as a guide for the correction instrument. Here again, an optimal connection between correction instrument and receiving device is guaranteed through the embodiment of the connecting device. The connecting device allows a one-dimensional relative movement between correction instrument and bone plate. In this manner a simple possibility is achieved that in all other directions, forces can be transferred from the correction instrument onto the bone plate. If the bone plate is bolted to the correction instrument, a force can also be transferred in the insertion direction.

In an improvement, it is provided that the correction instrument is embodied as essentially fork-shaped; when the correction element is slipped or set into place, the legs of the fork encompass or flank the receiving device for the fixing rod. A fork-shaped correction instrument has the essential advantage that it can encompass the receiving device in a simple manner and consequently can purposefully and reliably introduce correction forces onto it.

Preferably a correction rod can be inserted into and fastened in the correction instrument. The correction instrument can be connected, with or without the correction rod, to the bone plate or receiving device; it is preferable that the correction instrument first be fastened to the bone plate or receiving device, and that the correction rod then be inserted into the correction instrument and likewise fastened. Then the correction of the position of the individual holding apparatuses can take place via the correction rod or rods.

To increase primary stability, an improvement of the bone surgery holding apparatus according to the present invention is embodied so that in addition to the aforementioned fixing rod, a further fixing rod, if necessary with a smaller diameter, can be connected to the bone plate. The two fixing rods are disposed essentially parallel and form am H-frame. The fastening of the second fixing rod can be carried out for example directly on the plate and corresponds basically to the fixing of the aforementioned first fixing rod. A variant provides that in lieu of one of the two fastening screws, by way of which the bone plate is fastened to the bone, a bone screw with a forked head is used, by way of which not only is the bone plate fastened to the bone, but the fixing rod can also be inserted into this forked head and fastened. This screw thus serves both to fasten the holding apparatus according to the present invention and to fix the second fixing rod. This screw is preferably disposed on the dorsal side of the holding apparatus. The fastening of the fixing rod after being slipped in or inserted is carried out for example via a cap nut, but can also be carried out via an elongated end of the fixing device or the fixing plate; the elongated end protrudes beyond the receiving device and fits engagingly over the second fixing rod and holds it. This variant with an additional fixing rod can be realized in all embodiments of the bone surgery holding apparatus according to the present invention.

Preferably the receiving device has a basically rectangular outline. A correction instrument can easily contact and be fastened to a receiving device embodied in this way, for example by being slipped on or placed on.

The longitudinal axis of the receiving device preferably differs from the longitudinal axis of the bone plate by an angle other than 0°. In addition, the longitudinal axis of the bone plate can diverge from the longitudinal axis of the fixing rod, which can be inserted in the receiving device, by an angle other than 90°.

To reduce the overall height of the holding apparatus, the bottom of the receiving device for the fixing rod and the surface of the bone plate distal to the bone are disposed at least in part essentially in the same plane. Therefore the fixing rod is spaced from the surface of the bone via the bone plate.

In an improvement it is provided that the fixing device for the fixing rod has at least one support for at least one hook of the receiving device and that the fixing device can be suspended from the receiving device. To fasten the fixing device for the fixing rod to the receiving device, it can be screwed onto the receiving device. Preferably the fixing device has at least one captive screw.

In an improvement it is provided that the fixing device is embodied as a suspendable clamping cover. The suspended device has the advantage that the fixing device can be connected to the receiving device simply, without trouble, and quickly and can be fastened to it for example via a single screw; the fixing rod is clamped via the screw. Since only a single screw has to be attended to, the fixing rod can be more quickly fastened without trouble than in conventional holding apparatuses, which in particular shortens the time in surgery.

Captive screws are likewise preferable since with these, the operational risks are further reduced.

In a preferred exemplary embodiment, the bone plate has receptacles, disposed essentially diagonally, for fastening screws. The diagonal disposition reduces the overall length of the holding apparatus; the longitudinal axis of the receiving device is disposed in a diagonal extending in complementary fashion to it, as can be clearly seen from the drawing.

Further advantages, characteristics, and details of the present invention are related in the following description, in which particularly preferred exemplary embodiments are described individually with reference to the drawing. The characteristics shown in the drawing and in the description can be essential to the present invention either individually or in arbitrary combination.

DESCRIPTION OF THE PREFERRED EMBODIMENTS

Figure 1:
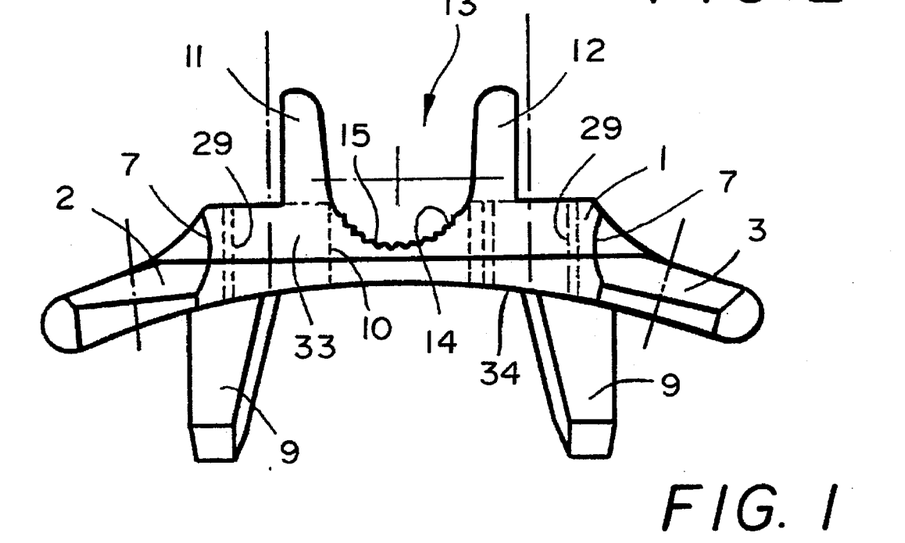
FIG. 1 shows a side view of a first embodiment of a bone plate of the holding apparatus according to the present invention.
Figure 4:
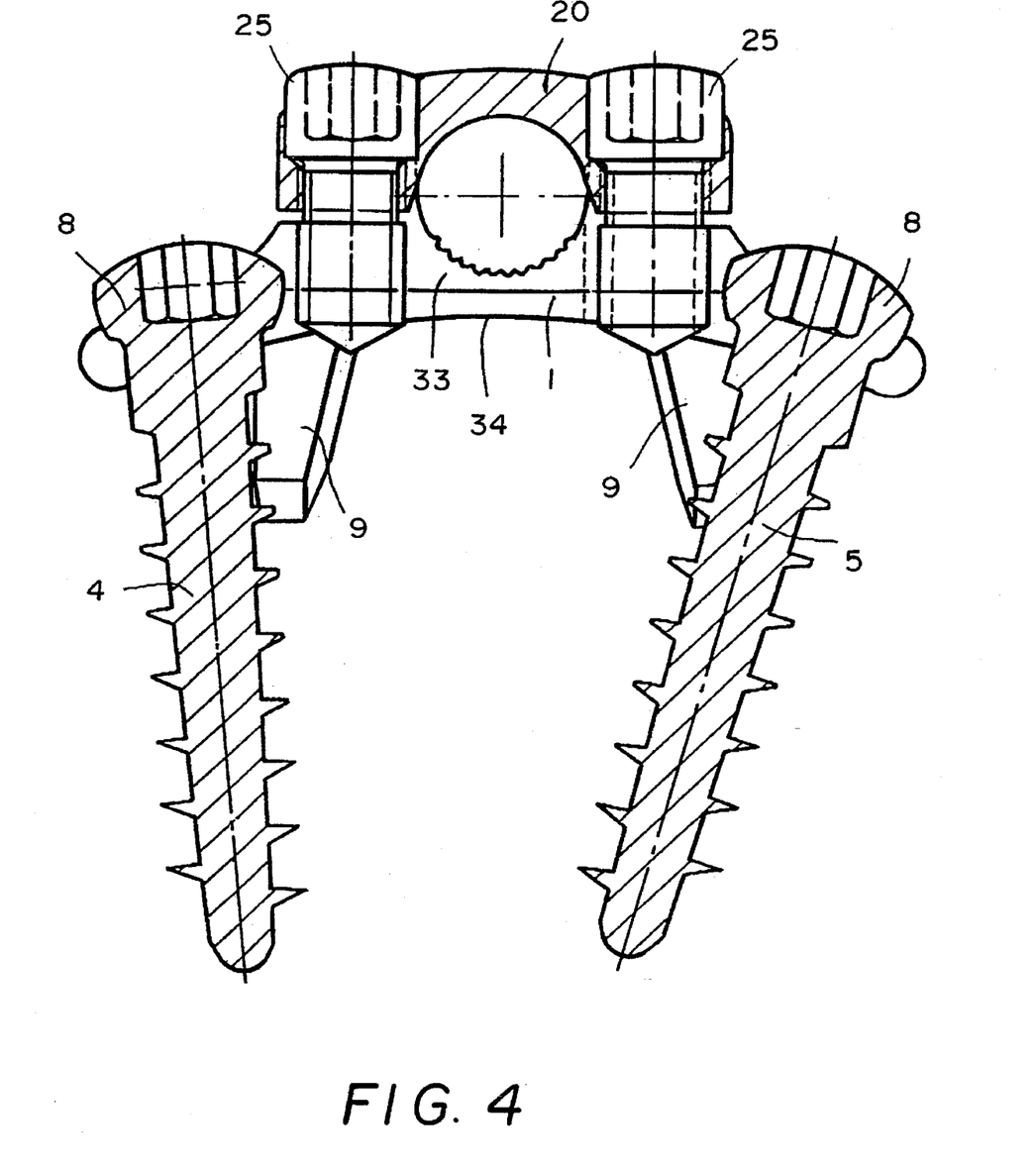
FIG. 4 shows a side view of the holding apparatus according to the present invention with a fixing plate screwed on the bone plate and with bone screws inserted into the bone plate.

FIG. 1 shows a side view of a bone plate 1 of a first exemplary embodiment; two fastening bores 2 and 3 can be seen, via which the bone plate 1 can be fastened to a bone, not shown, via suitable bone screws 4 and 5 (FIG. 4). Preferably the two fastening bores 2 and 3 are disposed opposite one another with regard to the center 6 (FIG. 5) of the bone plate 1. The fastening bores 2 and 3 each have a ball-shaped support 7, but this support can also be embodied conically. The head 8 of the bone screw 4 or 5, which is correspondingly spherically embodied, is received by this ball-shaped support 7. The support 7 has the advantage that the bone screw 4 or 5 does not necessarily have to be aligned coaxial to the fastening bore 2 or 3, but can assume slightly oblique positions so that the bone screw 4 or 5 can be screwed into suitable regions of the bone.

It can be further seen from FIGS. 1 and 4 that the fastening bore 2 is positioned obliquely; the axis of fastening bore 3 extends orthogonally to the bone plate 1, and the axis of fastening bore 2 extends essentially parallel to anchoring pins 9.

In FIG. 1 it is also clear to see that the bone plate 1 is provided with a central opening 10, which is circular in the exemplary embodiment shown in FIG. 1.

On the upper side of the bone plate 1, two forklike legs 11 and 12 are provided, which constitute a receiving device 13 for a fixing rod, not shown. This fixing rod can be inserted into the receiving device 13 between the two legs 11 and 12 and rests on the bottom 14. As can be clearly seen in FIG. 5, this bottom 14 is provided with longitudinal grooves 15, which engage complementary longitudinal grooves of fixing rod. These longitudinal grooves 15 are embodied without undercuts so that the fixing rod can be inserted into the receiving device 13 from above without trouble. The longitudinal grooves 15 prevent a rotation of the fixing rod in the receiving device 13. A trouble-free insertion of the fixing rod between the two legs 11 and 12 is made easier by the fact that they essentially form a conical insertion opening.

Figure 2:
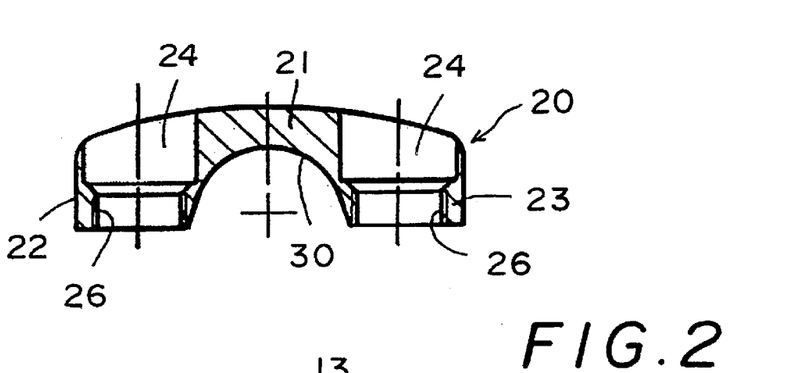
FIG. 2 shows a longitudinal section through a fixing plate.
Figure 3:
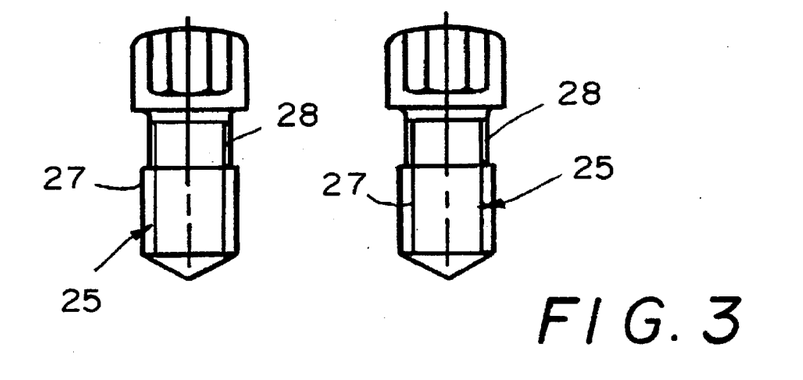
FIG. 3 shows screws for fastening the fixing plate to the bone plate.
Figure 5:
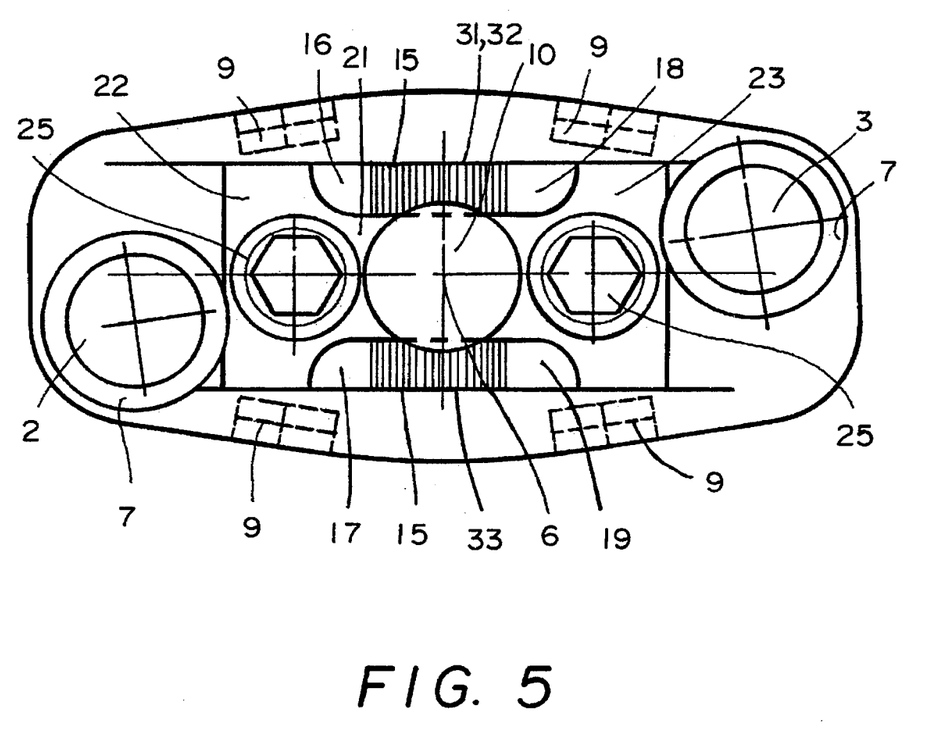
FIG. 5 shows a top view of the holding apparatus according to FIGS. 1–3.

In FIG. 5 it can be seen that the two legs 11 and 12 each comprise two prongs 16–19. These prongs 16–19 serve as a guide for a fixing plate 20, which is shown in FIG. 2. The fixing plate 20, viewed from above, has an H-shaped form, which is revealed in FIG. 5. If the fixing plate 20 is set upon the bone plate 1, then a strut 21 reaches through the empty space embodied between the two prongs, 16 and 17 or 18 and 19, and essentially bridges over the bearing region for the fixing rod. This strut 21 widens at its ends in such a way that it encompasses the prongs 16–19 on two sides. In addition, there are bores 24 disposed in both widened ends 22 and 23 for receiving screws 25, which are shown in FIG. 3.

These bores 24 are provided on their lower ends with a thread 26, by means of which captive holding is achieved for the screws 25. The two screws 25 have a thread 27, which is turned on a lathe in the upper region 28. If the screw 25 is situated in the bore 24 so that the region 28 is disposed in the region of the thread 26, the screw 25 can be rotated freely. It is then possible to screw the thread 27 into a thread 29 in the bone plate 1, so that the fixing plate 20 can be clamped onto a fixing rod.

The underside 30 of the fixing plate 20 can likewise be provided with longitudinal grooves in the region between the two bores 24. By means of this, a rotation of the fixing rod around its longitudinal axis is effectively prevented.

FIG. 4 shows a complete holding apparatus in which the fixing plate 20 is screwed onto the bone plate 1 by means of the screws 25. It can be clearly seen that since the fixing rod is inserted directly into the bone plate 1, the fixing forces can be introduced directly onto the bone plate 1 and from this via the anchoring pins 9 and the bone screws 4 and 5 onto the bone. In addition, a very low structural height is achieved since the fixing rod lies immediately on top of the bone surface. Coating of this holding apparatus with pleura can be done without trouble.

A further point essential to the present invention is seen in that the receiving device 13 has a tool engaging device 31 in the form of two faces 32 and 33, which are parallel to each other. The tool engaging device 31 is spaced apart from the bone surface so that the bone is not injured by the engaging tool. These faces 32 and 33 allow a tool, e.g. a suitably shaped fork or clamp, to effortlessly engage the bone plate 1. If the bone plate 1 is fastened onto a bone, then the bone plate 1 and with it the bone is brought into the desired position via the tool by means of a correction rod. After alignment of the bone plates 1, these are fixed in the predetermined position via the fixing rod, which is inserted into the respective receiving devices 13 and fastened there. Then the correction rod and the individual tools for aligning the bone plates 1 can be removed from the tool engaging device 31. Retention of the position of the bone plates 1 is guaranteed by means of the fixing rod. To reliably receive the forces that occur, this rod has a slightly larger diameter than in devices in which both a correction rod and a fixing rod are implanted.

It can also be clearly seen in FIGS. 1 and 4 that the contact face 34 of the bone plate 1 has a concave curvature whose course is steady and which approximately corresponds to the curvature of the bone surface. This guarantees a flush contact of the bone plate 1 with the bone surface, so that the forces of the bone plate 1 can be introduced onto the bone over a large area.

Figures 6, 7:
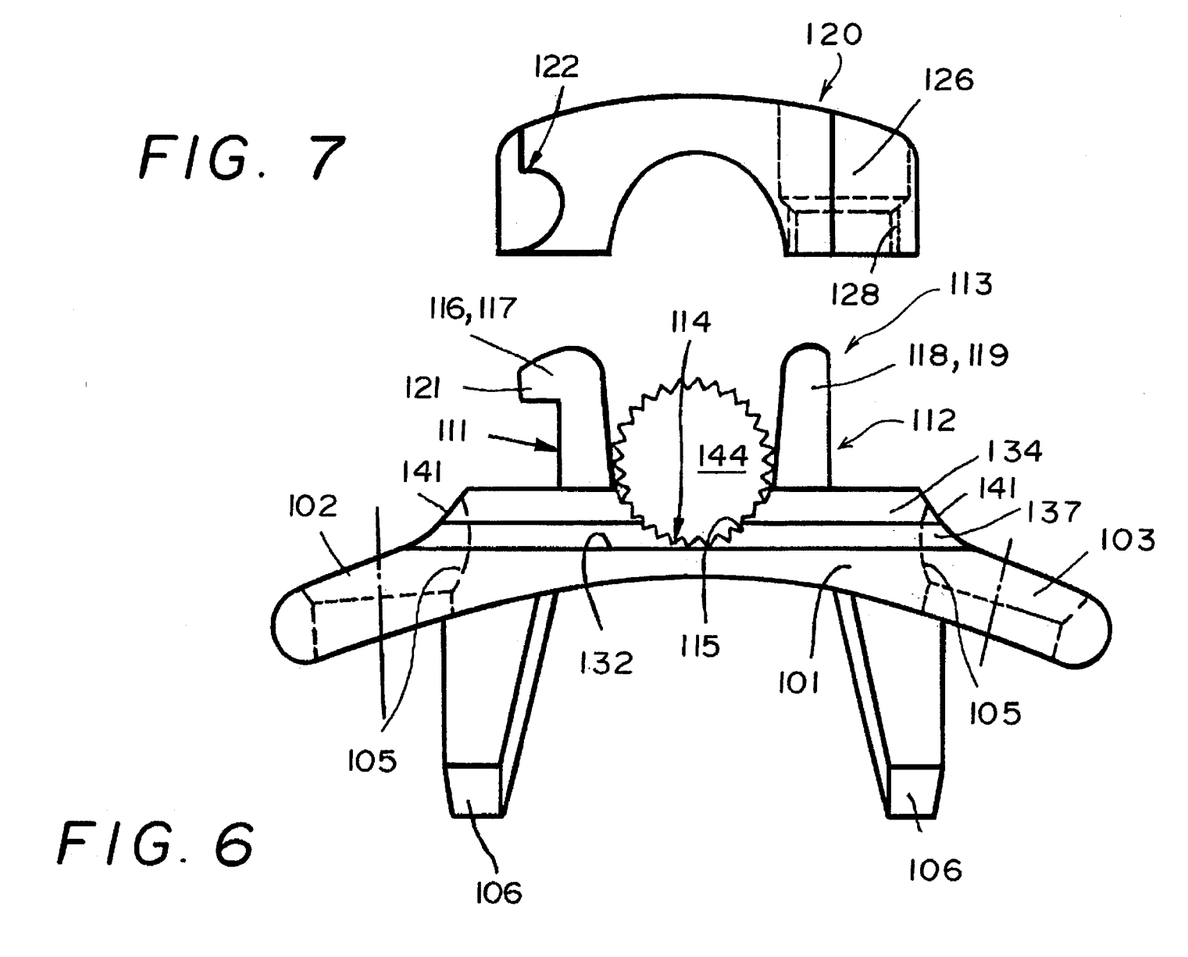
FIG. 6 shows a side view of a second embodiment of a bone plate of the present invention.
FIG. 7 shows a side view of the fixing device.

FIG. 6 shows a side view of a bone plate 101; two fastening bores 102 and 103 are shown with dashed lines, via which the bone plate 101 can be fastened to a bone, not shown, via suitable bone screws, likewise not shown. Preferably the two fastening bores 102 and 103 are disposed opposite each other with regard to the center 104 (see FIG. 9) of the bone plate 101. The fastening bores 102 and 103 each have a ball-shaped support 105, which however can also be embodied conically. The head of the bone screw, which is embodied correspondingly spherically, is received by this ball-shaped support 105. The support 105 has the advantage that the bone screw does not necessarily have to be aligned coaxial to the fastening bore 102 or 103, but can assume slightly oblique positions so that the bone screw can be screwed into suitable regions of the bone.

It can further be seen in FIG. 6 that the fastening bore 102 is disposed obliquely; the axis of the fastening bore 103 is orthogonal to the bone plate 101 or radial to its curvature, and the axis of fastening bore 102 extends essentially parallel to the anchoring pins 106. It can also be seen in FIG. 9 that the two fastening bores 102 and 103 are situated on a diagonal, which slopes counterclockwise with regard to the longitudinal axis 107 of the bone plate 101.

Figure 9:
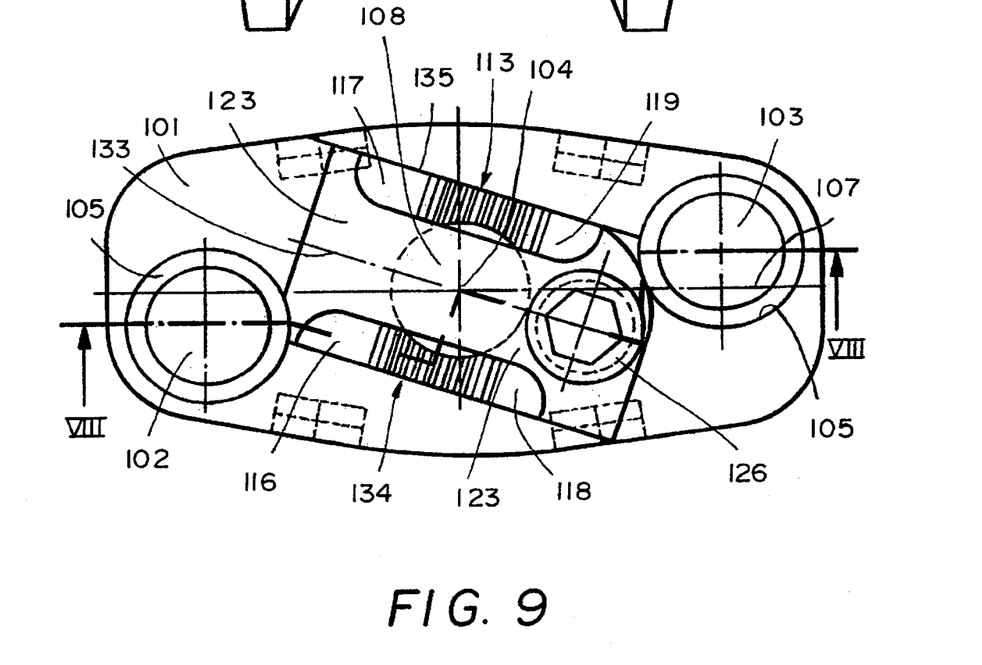
FIG. 9 shows a top view of the bone plate with fixing device.

Finally the bone plate 101, which can also be seen in FIG. 9, is provided with a central opening 108, which is essentially circular.

Figure 8:
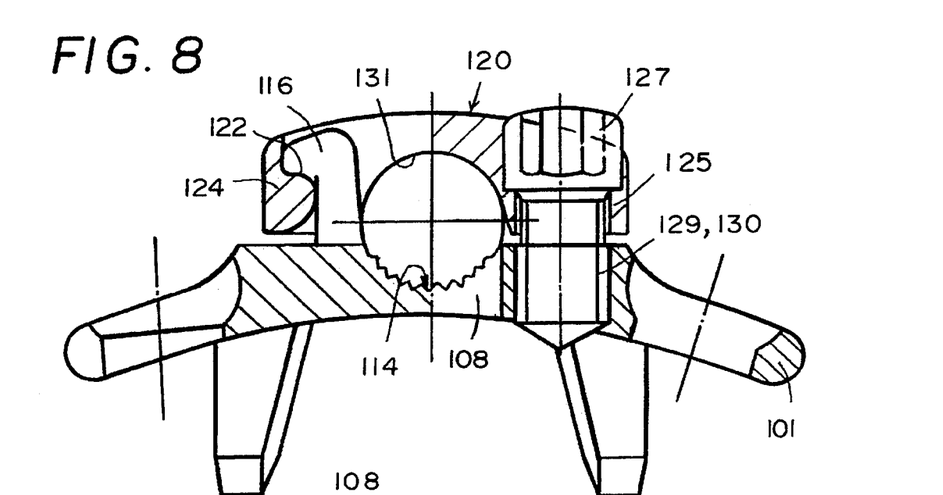
FIG. 8 shows a longitudinal section VIII—VIII according to FIG. 9 through the bone plate with fixing device in place.

On the upper side of the bone plate 101, two fork like legs 111 and 112 are provided, which constitute a receiving device 113 for a fixing rod, not shown. This fixing rod can be inserted into the receiving device 113 between the two legs 111 and 112 and rests on the bottom 114. This bottom 114, as can be clearly seen in FIGS. 6 and 8, is provided with longitudinal grooves 115, which engage the complementary longitudinal grooves of the fixing rod. These longitudinal grooves 115 are embodied without undercuts so that the fixing rod can be inserted into the receiving device 113 from above without trouble. The longitudinal grooves 115 prevent a rotation of the fixing rod in the receiving device 113. A trouble-free insertion of the fixing rod between the two legs 111 and 112 is also made easier by the fact that they essentially form a conical insertion opening.

In FIGS. 6 and 9 it can be seen that the two legs 111 and 112 each comprise two prongs 116–119. These prongs 116–119 serve both as a guide and a retainer for a fixing plate 120, which is shown in FIG. 7. The fixing plate 120, viewed from above, has an H-shaped form, which is seen in FIG. 9. To enable suspending the fixing plate 120 from the receiving device 113, the two prongs 116 and 117 are embodied as hook-shaped and have a projection 121 protruding radially outward on their distal free end. To receive this projection 121, the fixing plate 120 is provided with an undercut 122 on each of the free ends of one of its H-legs 124, from which undercut 122 the projection 121 can be suspended, as shown in FIG. 8. If the fixing plate 120 is suspended from the prongs 116 and 117 and, via the joint formed by the projections 121 and undercuts 122, is placed clockwise onto the bone plate 101, then a strut 123 reaches through the empty space formed between the two prongs 116 and 117 as well as 118 and 119 and essentially bridges over the bearing region for the fixing rod. This strut 123 widens at its ends in such a way that it encompasses the prongs 116 and 117, or engages them from behind, with the H-leg 124 (FIG. 8) and encompasses the two prongs 118 and 119, or engages them from behind, with the H-leg 125 (FIG. 8).

In the strut region disposed on the H-leg 125, in addition there is a bore 126, which serves to receive a screw 127, which is shown in FIG. 8. This bore 126 is provided on its lower end, i.e. on its end oriented toward the bone plate 101, is provided with a thread 128, by means of which a captive holding is achieved for the screw 127. The screw 127 likewise has a thread 129, which is turned on a lathe in the upper region.

If the screw 127 is situated in the bore 126 so that the lathe-recessed region comes to rest in the thread 128 of the fixing plate 120, then the screw 127 can be unscrewed. The screw 127 can then be screwed into a thread 130 in the bone plate 101, so that the fixing plate 120 can be clamped onto a fixing rod; the fixing plate 120 is pivoted clockwise around the joint formed by the projection 121 and the undercut 122.

The underside 131 of the fixing plate 120 can likewise be provided with longitudinal grooves (not shown) in the region between the prongs 116–119. By means of this, an additional rotation prevention is achieved for the fixing rod 144 around its longitudinal axis.

It can also be clearly seen in FIGS. 6 and 8 that the bottom 114 of the receiving device 113 is disposed on the plane 132 of the bone plate 101 so that the fixing rod 144 is disposed with a minimal spacing from the bone surface and the entire holding apparatus has a low structural height.

It can be seen in FIG. 9 that the receiving device 113 is disposed on the distal side of the bone plate 101 in such a way that the longitudinal axis 133 extends diagonally on the distal upper end of the bone plate 101, i.e. is rotated clockwise with regard to the longitudinal axis 107 of the bone plate 101. The rotation of the longitudinal axis 133 of the receiving device 113 and the diagonals, in which the two fastening bores 102 and 103 are disposed, are rotated in different directions with regard to the longitudinal axis 107 of the bone plate 101. In this manner, a short structural length of the bone plate 101 is achieved.

Figure 10:
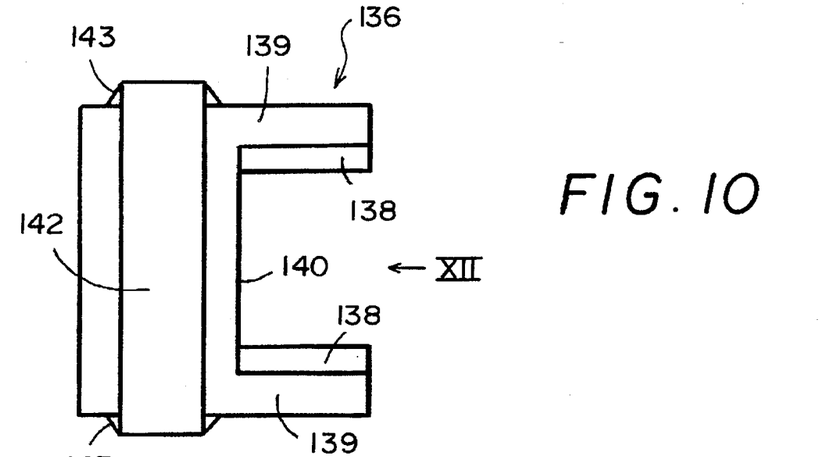
FIG. 10 shows a top view of a detached correction instrument.
Figure 11:
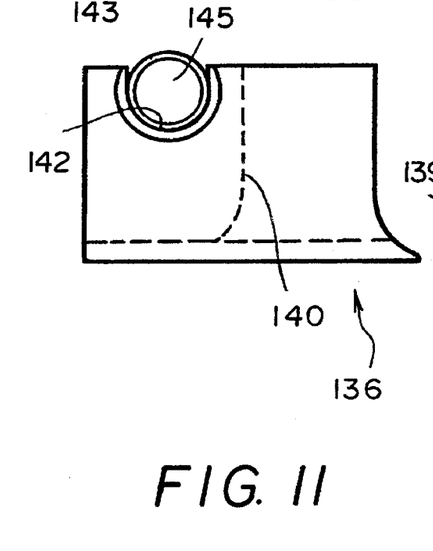
FIG. 11 shows a side view of the correction instrument according to FIG. 10.
Figure 12:
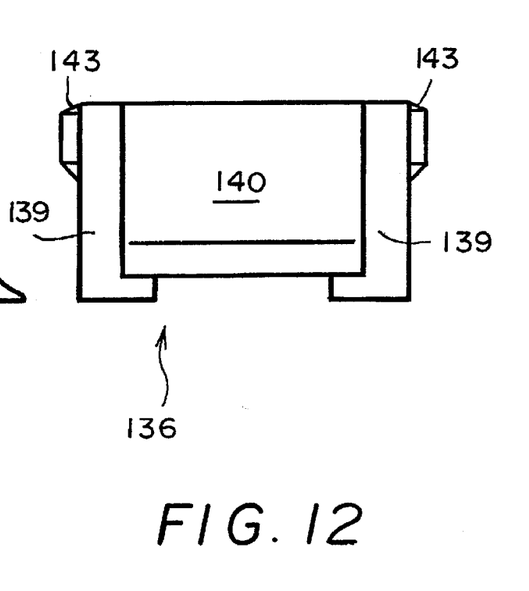
FIG. 12 shows a view in the direction of the arrow XII according to FIG. 10.

It can also be seen in FIGS. 6 and 9 that the receiving device 113 has parallel side faces 134 and 135, which serve to receive a correction instrument 136, which is shown in FIGS. 10–12. The two side faces 134 and 135 are each provided with a longitudinal groove 137, which is engaged by projections 138 of two fork legs 139. The inner faces of the fork legs 139 are spaced apart from one another at such a distance that they are just able to receive the receiving device 113. The wall 140 serves as a stop for limiting insertion of the correction instrument 136 and contacts 141 when the instrument is slipped on. In addition, the correction instrument 136 has an essentially U-shaped recess 142, into which a correction rod (threaded rod) can be inserted. The ends of the recess 142 are provided with conically tapering projections 143, which extend in a circle around the rim of the recess 142. These projections 143 serve to receive a fastening nut for the correction rod; the fastening nut (not shown) has a correspondingly conical recess. Nuts of this kind are known.

After fastening the bone plate 101 to the surface of the bone to be corrected, e.g. a vertebrae, the correction instrument 136 is slipped onto the receiving device 113. In the event that there are several bone plates 101, a corresponding number of correction instruments 136 are slipped on. Now a correction rod 145 is inserted into the individual correction instruments 136 and fastened via the nuts on the projections 143. By rotating the nuts, the position of the correction instrument 136 can be adjusted with regard to correction rod 145 and consequently the position of the bone plate 101, and with it the vertebra, can be adjusted. If the individual correction plates assume the desired position, then a fixing rod 144 is inserted in the individual receiving devices 113 of the bone plates 101 and fixed with the fixing device 120, which is first suspended and then fastened with the screw 127. Then the individual bone plates 101 are fixed to one another, the nuts of the correction rod are loosened, the correction rod 145 is taken out, and the individual correction instruments 136 are removed. Thus the correction rod 145 and the correction instruments 136 are not implanted in the body of the patient.

The holding apparatus according to the present invention has an extremely low structural height and compared to conventional holding apparatuses is light and nevertheless stable.

We claim:

1. A bone surgery holding device for a fixing rod, comprising:
   a bone plate for fastening to a bone;
   a fixing plate; and
   at least one screw for securing said fixing plate to said bone plate, wherein:
   said bone plate and said fixing plate define a receiving device for receiving the fixing rod;
   said bone plate has a longitudinal axis and includes a contact surface adapted to fit the surface of a bone; and
   said receiving device has a longitudinal axis and is adapted so that the fixing rod can be received in said receiving device after said fixing plate is fastened to a bone.

2. The bone surgery holding device according to claim 1, wherein said receiving device is embodied as fork-shaped and has two distally protruding legs.

3. The bone surgery holding device according to claim 2, wherein each leg of said receiving device includes two prongs, which serve as a guide for said fixing plate.

4. The bone surgery holding device according to claim 3, wherein an empty space exists between said two prongs, in which space said fixing plate is guided so that it can move in the direction of said bone plate.

5. The bone surgery holding device according to claim 3, wherein said prongs fix said fixing plate in the horizontal plane.

6. The bone surgery holding device according to claim 3, wherein said fixing plate can be fastened with respect to said bone plate via fastening devices.

7. The bone surgery holding device according to claim 6, wherein said fastening devices comprise two screws.

8. The bone surgery holding device according to claim 7, wherein said screws are fastened to said fixing plate in captive fashion.

9. The bone surgery holding device according to claim 7, wherein said screws are disposed in the longitudinal axis of said fixing plate.

10. The bone surgery holding device according to claim 3, wherein said fixing plate, at least in part, has a profiling on its side oriented toward the fixing rod.

11. The bone surgery holding device according to claim 1, wherein said receiving device is open distally.

12. The bone surgery holding device according to claim 1, wherein said receiving device is provided with a tool engaging device on which a tool can be placed to position said bone plate.

13. The bone surgery holding device according to claim 12, wherein said tool engaging device is embodied by two parallel faces.

14. The bone surgery holding device according to claim 13, wherein the faces of said tool engaging device are provided on said receiving device.

15. The bone surgery holding device according to claim 13, wherein a fork-shaped tool can be slipped onto the faces of said tool engaging device and removed after the position correction of said bone plate.

16. The bone surgery holding device according to claim 1, wherein said receiving device is embodied to receive a longitudinally grooved fixing rod with a diameter of 6 mm.

17. The bone surgery holding device according to claim 1, wherein said holding device has a height of 8 mm.

18. The bone surgery holding device according to claim 1, wherein said bone plate includes two fastening bores by which said bone plate is fastened to a bone, and wherein said receiving device is provided between said two fastening bores.

19. The bone surgery holding device according to claim 18, wherein each fastening bore has a conical seat for a bone screw.

20. The bone surgery holding device according to claim 1, wherein said bone plate is constructed mirror symmetrically.

21. The bone surgery holding device according to claim 1, wherein said bone plate has a connecting device for a correction instrument, which includes at least one correction rod.

22. The bone surgery holding device according to claim 21, wherein said correction instrument can be inserted into or onto said connecting device.

23. The bone surgery holding device according to claim 22, wherein the insertion axis essentially corresponds to the longitudinal direction of said bone plate.

24. The bone surgery holding device according to claim 22 wherein said correction instrument has a stop that serves as an insertion limiter.

25. The bone surgery holding device according to claim 22, wherein said connecting device includes a first part provided on said correction instrument and a second part provided on said bone plate, and wherein said two parts comprises a tongue-and-groove connection.

26. The bone surgery holding device according to claim 21 wherein said connecting device is provided on said receiving device for the fixing rod.

27. The bone surgery holding device according to claim 21 wherein said connecting device is embodied by two parallel faces.

28. The bone surgery holding device according to claim 27, wherein at least one of the faces is provided with a groove extending in the insertion direction, which serves as a guide for said correction instrument.

29. The bone surgery holding device according to claim 21, wherein said connecting device allows a one-dimensional relative movement between said correction instrument and said bone plate.

30. The bone surgery holding device according to claim 21 wherein said correction instrument is embodied as essentially fork-shaped, wherein when said correction instrument is placed on said connecting device, the fork legs encompass or flank said receiving device for the fixing rod.

31. The bone surgery holding device according to claim 21, wherein a correction rod can be inserted into and fastened in said correction instrument.

32. The bone surgery holding device according to claim 21, wherein said receiving device has an essentially rectangular-shaped outline.

33. The bone surgery holding device according to claim 32, wherein the longitudinal axis of said receiving device differs from the longitudinal axis of said bone plate by an angle other than 0°.

34. The bone surgery holding device according to claim 21, wherein the longitudinal axis of said bone plate can diverge by an angle other than 90° from the longitudinal axis of the fixing rod, which can be inserted into said receiving device.

35. The bone surgery holding device according to claim 21, wherein the bottom of said receiving device and the surface of said bone plate distal to the bone, at least in part, lie essentially in the same plane.

36. The bone surgery holding device according to claim 21, wherein said fixing plate for the fixing rod has at least one support for at least one hook of said receiving device, and wherein said fixing plate can be suspended from said receiving device.

37. The bone surgery holding device according to claim 21, wherein said fixing plate for the fixing rod can be screwed onto said receiving device.

38. The bone surgery holding device according to claim 37, wherein said fixing plate has at least one captive screw.

39. The bone surgery holding device according to claim 21, wherein said fixing plate is embodied as a suspendable clamping cover.

40. The bone surgery holding device according to claim 21, wherein said bone plate has two diagonally disposed fastening bores.

41. The bone surgery holding device according to claim 21, wherein said fixing plate can be removed from said receiving device or said bone plate.

42. The bone surgery holding device according to claim 21, wherein said fixing plate is connected via a support to said receiving device or said bone plate.

* * * * *